(12) United States Patent
Jun et al.

(10) Patent No.: US 9,557,324 B2
(45) Date of Patent: Jan. 31, 2017

(54) CONJUGATE OF A METAL NANOPARTICLE AND A LIGHT EMITTING MATERIAL

(71) Applicants: SAMSUNG ELECTRONICS CO., LTD., Suwon-si, Gyeonggi-do (KR); THE REGENTS OF THE UNIVERSITY OF CALIFORNIA, Oakland, CA (US)

(72) Inventors: Shin Ae Jun, Seongnam-si (KR); Dae ha Seo, San Francisco, CA (US); Eun Joo Jang, Suwon-si (KR); Young-Wook Jun, San Francisco, CA (US)

(73) Assignees: SAMSUNG ELECTRONICS., LTD., Gyeonggi-do (KR); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/184,469

(22) Filed: Feb. 19, 2014

(65) Prior Publication Data

US 2014/0295410 A1 Oct. 2, 2014

Related U.S. Application Data

(60) Provisional application No. 61/766,306, filed on Feb. 19, 2013.

(51) Int. Cl.
*C12M 1/36* (2006.01)
*G01N 21/00* (2006.01)
(Continued)

(52) U.S. Cl.
CPC ............ *G01N 33/52* (2013.01); *G01N 33/582* (2013.01); *G01N 33/587* (2013.01); *G01N 33/588* (2013.01); *Y10T 436/143333* (2015.01)

(58) Field of Classification Search
None
See application file for complete search history.

(56) References Cited

U.S. PATENT DOCUMENTS 7,459,145 B2 * 12/2008 Bao .................... A61K 49/0002
424/1.11
8,841,085 B2 9/2014 Kwon et al.
(Continued)

FOREIGN PATENT DOCUMENTS

KR 1020100026477 3/2010
KR 1020110039170 4/2011

OTHER PUBLICATIONS

Ming Li, et al., "Detection of Mercury(II) by Quantum Dot/DNA/Gold Nanoparticle Ensemble Based Nanosensor Via Nanometal Surface Energy Transfer",Analytical Chemistry, vol. 83,2011, pp. 7061-7065.
(Continued)

*Primary Examiner* — Betty Forman
(74) *Attorney, Agent, or Firm* — Cantor Colburn LLP

(57) ABSTRACT

Disclosed are a conjugate of a metal nanoparticle including a magnetic core and at least one light emitting material linked to the metal nanoparticle through a linker, wherein the linker has an affinity for a biological material and has changed structure after contacting a biological material, a biosensor including the conjugate, and a method of measuring a concentration of specific biological material in a biological sample using the conjugate or the biosensor.

25 Claims, 7 Drawing Sheets

(51) Int. Cl.
*G01N 33/52* (2006.01)
*G01N 33/58* (2006.01)

(56) References Cited

U.S. PATENT DOCUMENTS

| | | |
|---|---|---|
| 2002/0034747 A1* | 3/2002 | Bruchez et al. .................. 435/6 |
| 2002/0177143 A1* | 11/2002 | Mirkin et al. .................... 435/6 |
| 2005/0074779 A1* | 4/2005 | Vo-Dinh ............................ 435/6 |
| 2005/0130167 A1* | 6/2005 | Bao .................... A61K 49/0002 |
| | | 435/6.12 |
| 2006/0183247 A1 | 8/2006 | Kim et al. |
| 2010/0129808 A1* | 5/2010 | Mirkin et al. .................... 435/6 |
| 2011/0084199 A1 | 4/2011 | Pyo |
| 2013/0040292 A1* | 2/2013 | Fernandez Lopez |
| | | et al. ............................ 435/6.11 |

OTHER PUBLICATIONS

Wang Yu-Hong, et al., "A quantum dots and superparamagnetic nanoparticle-based method for the detection of HPV DNA", Nanoscale Research Letters, 2011, vol. 6, No. 461, pp. 1-9.

Xiuling Wang, et al.,"A Novel CdSe/CdS Quantum Dot-based Competitive Fluoroimmunoassay for the Detection of Clenbuterol Residue in Pig Urine Using Magnetic Core/Shell Fe3O4/Au Nanoparticles as a Solid Carrier",Analytical Sciences,Dec. 2009, vol. 25.

Yang Xu, et al., "Multifunctional Fe3O4 Cored Magnetic-Quantum Dot Fluorescent Nanocomposites for RF Nanohyperthermia of Cancer Cells", J. Phys. Chem., vol. 114, pp. 5020-5026, 2010.

\* cited by examiner (a)                       (b)

CONJUGATE OF A METAL NANOPARTICLE AND A LIGHT EMITTING MATERIAL

CROSS-REFERENCE TO RELATED APPLICATION

This application claims priority to and the benefit of U.S. Provisional Application No. 61/766,306 filed with the United States Patent Trademark Office on Feb. 19, 2013, the entire contents of which are incorporated herein by reference.

BACKGROUND

1. Field of the Invention

A conjugate of a metal nanoparticle and a light emitting material, and a use thereof, are disclosed.

2. Description of the Related Art

Resonance of absorbing light at a specific wavelength and have a large extinction coefficient (about $10^5$ cm$^{-1}$M$^{-1}$). Accordingly, when the metal nanoparticles are used as an energy transfer acceptor, the sensor including the metal nanoparticles may have sensitivity at a monomolecular level and also an improved transfer-energy rate and increased working distance.

In addition, metal particles have additional merits of being stable and not being photobleached.

On the other hand, a disease may be diagnosed early by detecting a biomarker related to the disease such as genes, proteins, enzymes, antigens, antibodies, and the like at a low concentration existing in a biological sample such as bloods, saliva, or the like. Accordingly, the detection needs a very sensitive biosensor.

A conventional method of detecting genes, proteins, enzymes, antigens, antibodies, and the like in a biological sample may include gel electrophoresis, multistep liquid chromatography, enzyme-linked immunosorbent assay (ELISA), or a method of measuring a peak shift through spectroscopy by binding a phosphor with a peptide substrate specifically degraded in a protein degrading enzyme. However, these methods need multistep protocols and thus are not economically and timely efficient for screening many drugs to develop a new medicine. In addition, these methods may not be used for early diagnosis of a disease by detecting expression of a specific biomarker in vivo or quantitatively measuring the amount of the expression.

Accordingly, a more sensitive biosensor capable of detecting expression of a specific biomarker in vivo and quantitatively analyzing the amount of the expression is required.

SUMMARY

In one embodiment, a conjugate of a metal nanoparticle and a light emitting material being capable of detecting existence of a biological material with high sensitivity is provided.

In another embodiment, a biosensor including the conjugate of a metal nanoparticle and a light emitting material is provided.

In yet another embodiment, a method of detecting a biological material in a biological sample using the conjugate or the biosensor is provided.

One embodiment of the present invention provides a conjugate of a metal nanoparticle and a light emitting material that includes a metal nanoparticle including a magnetic core,
a light emitting material, and
a linker that links the metal nanoparticle to the light emitting material and has an affinity for a biological material.

The light emitting material may be a semiconductor nanocrystal, a fluorescent dye, a dye-doped transparent metal oxide, a lanthanide, or a mixture thereof.

The dye-doped transparent metal oxide may be dye-doped silica ($SiO_2$), dye-doped titania ($TiO_2$), dye-doped alumina ($Al_2O_3$), or dye-doped zirconia ($ZrO_2$).

The light emitting material may have a diameter ranging from about 2 nm to about 30 nm.

The metal nanoparticle may further include a metal shell formed on the surface of the magnetic core.

The metal shell may be a metal shell having Plasmon characteristics selected from gold, silver, copper, platinum, or an alloy thereof.

The metal nanoparticle may further include a dielectric layer including a metal oxide or a polymer interposed between the magnetic core and the metal shell.

The metal oxide may be selected from $SiO_2$, $TiO_2$, $ZrO_2$, $Al_2O_3$, $Cu_xO$ (0<x<2), and a combination thereof.

The magnetic core may be iron (Fe), cobalt (Co), iron oxide, cobalt oxide, manganese oxide, zinc oxide, or an alloy thereof, or a core/shell structure of the foregoing materials. The magnetic core may be an iron/zinc oxide core.

The metal nanoparticle may have a diameter of about 5 nm to about 200 nm, and the magnetic core may have a diameter of about 2 nm to about 180 nm.

In the conjugate, the linker may have a structure that is changed in contact with the biological material. For example, a part of the linker may be cleaved or a bent part of the linker may be unfolded in contact with a specific biological material so that a distance between the metal nanoparticle and the light emitting material may become far away from each other. In addition, the unfolded linker may be bent to become short or folded in contact with a specific biological material so that a distance between the metal nanoparticle and the light emitting material may become closer to each other.

The linker may be DNA, single strand DNA (ssDNA), RNA, a protein, a peptide, an antigen, an antibody, an enzyme, a hydrocarbon material (a carbohydrate), a part thereof, or a combination thereof. The linker may be a DNA having a hairpin structure.

Specific biological material being capable of being bound with the linker may be an enzyme, an antigen, an antibody, a protein, a peptide, DNA, single stranded, RNA, a hydrocarbon material (a carbohydrate), a fragment thereof, or a combination thereof.

The biological material may be a biomarker of a disease.

The linker may be about 3 nm to about 100 nm long.

The linker may have both terminal ends respectively substituted with a functional group capable of being bound with the metal nanoparticle and with the light emitting material.

One terminal end of the linker for binding the metal nanoparticle may be substituted with thiol, thioether, thiourea, phosphorothiate, thiocarbamate, amine, histidine, phosphine, a phosphite residual group, and the like.

The other terminal end of the linker for binding the light emitting material may be may be substituted with biotin, avidin, histag, Ni-NTA (nickel nitrile triacetic acid), N-hydroxyl succinmide, amine, thiol, histidine, phosphine, an aldehyde tag, a hydrazide tag, a halide, an alkyne, an azide, a halotag, benzyl guanine, a sanp tag, benzyl cytosine, a CLIP-tag, FlAG-tag, or maleimide.

On the other hand, the light emitting material may be coated with biotin, avidin, HIS-tag, Ni-NTA(Nickel Nitrilotriacetic acid), N-hydroxysuccinmide, amine, thiol, histidine, phosphine, aldehyde tag, hydrazide tag, halide, alkyne, azide, Halo tag, benzylguanine, SNAP-tag, benzylcytosine, CLIP-tag, FLAG-tag, or maleimide, in order to be linked with the linker.

Another embodiment of the present invention provides a biosensor including the conjugate of a metal nanoparticle and a light emitting material is provided.

The biosensor may further include a substrate supporting the conjugate of a metal nanoparticle and a light emitting material.

The substrate may be transparent or opaque, and may be made of an inorganic material or an organic material.

The transparent substrate may include an inorganic material substrate such as glass, ITO (Indium Tin Oxide), quartz, silicon, alumina, or carbon materials, or an organic material substrate made of a transparent polymer. The opaque substrate may include a paper, an opaque glass, or an opaque polymer substrate.

The conjugate of a metal nanoparticle and a light emitting material may be supported by a substrate by being bound with the substrate.

The conjugate of a metal nanoparticle and a light emitting material may be bound with the substrate by a chemical reaction or magnetism.

In another embodiment of the present invention, provided is a method of measuring the concentration of a specific biological material in a biological sample, which includes contacting the conjugate of a metal nanoparticle and a light emitting material or biosensor according to the embodiment with the biological sample.

The method of measuring the concentration of a biological material may further include measuring light emission or light absorption of the light emitting material after contacting the conjugate or the biosensor with the biological sample.

The method of measuring the concentration of a biological material may further include concentrating the conjugate or the biosensor using magnetism, before measuring light emission or light absorption of the light emitting material.

The biological material may be an enzyme, an antigen, an antibody, a protein, a peptide, a hydrocarbon material (a carbohydrate), DNA, RNA, a part thereof, or a combination thereof, and for example, a biomarker of a disease.

The method may be performed in vitro or in vivo.

DETAILED DESCRIPTION

Figure 1:
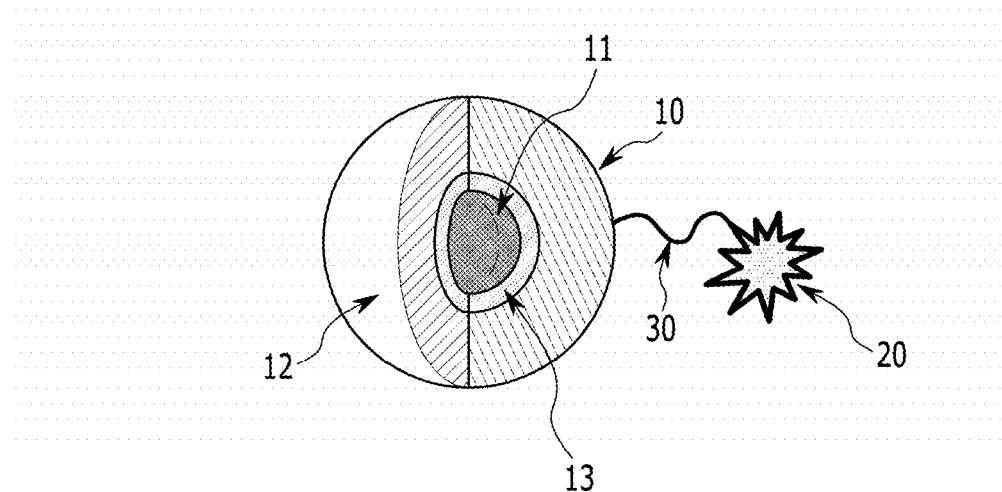
FIG. 1 is a schematic view showing a conjugate of a metal nanoparticle (10) including a magnetic core (11) and a light emitting material (20) linked with a linker (30) according to one embodiment.

This disclosure will be described more fully hereinafter in the following detailed description, in which some but not all embodiments of this disclosure are described. This disclosure may be embodied in many different forms and is not be construed as limited to the embodiments set forth herein; rather, these embodiments are provided so that this disclosure will satisfy applicable legal requirements.

In one embodiment of the present invention, provided is a conjugate of a metal nanoparticle and a light emitting material that includes
a metal nanoparticle including a magnetic core,
a light emitting material, and
a linker that links the metal nanoparticle to the light emitting material and has an affinity for a biological material.

A FRET (Fluorsence Resonance Energy Transfer) sensor including a conjugate of a metal nanoparticle and a light emitting material has increased working distance and an excellent fluorescence extinction rate compared to the conventional FRET sensor, and also has advantages of the metal particle being stable and of no photo bleaching.

In the embodiment, the metal nanoparticle is a metal nanoparticle including a magnetic core, wherein the metal is included in a form of a metal shell on the magnetic core.

When the metal nanoparticle includes a metal shell formed on the surface of the magnetic core surface, a plasmon resonance frequency may be adjusted to be desirable by controlling the thickness of the metal shell. That is to say, light in a red region is absorbed when the shell is thin, multiplexing detection may be possible.

In addition, since the metal nanoparticle includes the magnetic core inside the metal shell, the conjugate including the metal nanoparticle and a particle to bind with the conjugate may be concentrated and separated using a magnetic field of a particle magnetic core. The linker used to link the metal nanoparticle with the light emitting material has affinity for a biological material, and particularly, when the linker contacts a specific biological material, a structure of the linker may be changed. For example, when the linker contact a specific biological material, a part of the linker may be cleaved or a part of a bent linker may be unfolded. Alternatively, the unfolded linker may be bent to be short or may be folded when it contacts a specific biological material.

Accordingly, in case that a part of the linker is cleaved or a part of a bent linker is unfolded when it contacts a specific biological material, in the conjugate including such a linker, the light emitting material may be close to the metal nanoparticle when the conjugate does not contact a specific biological material, while the light emitting material may become far away from the metal nanoparticle when the conjugate contacts a specific biological material Herein, the metal nanoparticle may include a metal shell formed of a metal selected from gold, silver, copper, platinum, or an alloy thereof and having plasmon characteristics. Accordingly, when the light emitting material is close to the metal nanoparticle, the metal nanoparticle absorbs all the fluorescence emitted from the light emitting material, and thus, fluorescence is not emitted. However, when the conjugate contacts the specific biological material, the metal nanoparticle becomes far away from the light emitting material, and thus the light emitting material emits fluorescence.

In other words, when the metal nanoparticle is close to the light emitting material, light emission of the light emitting material is quenched. However, the light emitting material has a fluorescence resonance energy transfer (FRET) such that the light emitting material emits light when it becomes far away from the light emitting material, and thus, may show a binding degree of the conjugate with the specific biological material.

In case that the unfolded linker is bent to become short and folded when it contacts a specific biological material, in the conjugate including such a linker, the light emitting material may become far away from the metal nanoparticle when the conjugate does not contact a specific biological material, while the light emitting material may be close to the metal nanoparticle when the conjugate contacts a specific biological material. In this case, the light emitting material of the conjugate may emit light when the conjugate does not contact a specific biological material, while light emission disappear when the conjugate contacts a specific biological material.

On the other hand, as described above, the conjugate includes a magnetic core inside the metal nanoparticle and may be easily separated or concentrated in a solution using magnetic force from the magnetic core. Accordingly, even when the biological material exists at a very low concentration, the conjugate boned with such a biological material may be both easily concentrated and separated, and thereby the biological material at a low concentration may be easily measured and analyzed at a monomolecular level.

The magnetic core in the metal nanoparticle may be an iron-containing magnetic core. For example, the magnetic core may be iron (Fe), cobalt (Co), iron oxide, cobalt oxide, manganese oxide, zinc oxide, or an alloy thereof, or a core/shell thereof. For example, the magnetic core may be an iron/zinc oxide core.

The metal nanoparticle may further include a dielectric layer including a metal oxide selected from $SiO_2$, $TiO_2$, $ZrO_2$, $Al_2O_3$, $Cu_xO$ ($0<x<2$), or a combination thereof, or a polymer between the magnetic core and the metal shell. When the conjugate further includes the dielectric layer of a metal oxide layer or a polymer layer between the magnetic core and the metal shell, characteristics of the magnetic core and metal shell may be better maintained.

The metal nanoparticle may have a diameter of about 5 nm to about 200 nm, and the magnetic core therein may have a size of about 2 nm to about 180 nm.

The light emitting material may include a semiconductor nanocrystal, a fluorescent dye, a dye-doped transparent metal oxide, a lanthanide, or a combination thereof. The light emitting material may be, for example, a semiconductor nanocrystal in terms of luminous efficiency and sensitivity.

In one exemplary embodiment, the light emitting material may be a fluorescent dye. The fluorescent dye may be selected from fluorescein, rhodamines, eosines, alexas, and rose bengal, but may include any fluorescent material without any particular limit.

In one exemplary embodiment, the light emitting material may be a dye-doped transparent metal oxide. The transparent metal oxide may be, for example, dye-doped $SiO_2$, dye-doped $TiO_2$, dye-doped $Al_2O_3$, or dye-doped $ZrO_2$, but is not limited thereto. The dye-doped transparent metal oxide may be manufactured in a form of a bead by mixing the fluorescent dye and the transparent metal oxide.

The semiconductor nanocrystal may be any well-known semiconductor nanocrystal in this art, and may be anything that displays fluorescence in a near infrared ray region. For example, the semiconductor nanocrystal may be selected from a Group II-VI compound, a Group III-V compound, a Group IV-VI compound, a Group IV element, a Group IV compound, and a combination thereof.

The semiconductor nanocrystal may be formed of a single element or a binary compound, a ternary element compound, or a quaternary element compound. When formed of a compound of more than two elements, these elements respectively exist in a uniform concentration in the semiconductor nanocrystal particle or partially different concentrations in the same particle. In addition, the semiconductor nanocrystal may have a core/shell structure in which one semiconductor nanocrystal surrounds another semiconductor nanocrystal. Herein, the elements in the shell may have a concentration gradient such that their concentration becomes gradually lower in the interface of the shell with the core.

The light emitting material may have a diameter of about 2 nm to about 30 nm.

The linker may be DNA, single strand DNA, RNA, a protein, a peptide, an antigen, an antibody, an enzyme, a carbohydrate, a fragment thereof, or a combination thereof, but is not limited thereto. In an exemplary embodiment, the linker may be DNA having a hairpin structure, or single strand DNA.

The linker has affinity for a biological material such as an enzyme, an antigen, an antibody, a protein, a peptide, a hydrocarbon material (a carbohydrate), DNA, RNA, or a part thereof, and may be, for example, bound with the biological material.

The biological material may be, for example, a biomarker of a disease, and is not limited to the aforementioned foregoing materials.

The biological material and the linker may have affinity for each other, and for example, the linker may be any material being capable of changing the structure in contact with the biological material.

The biological material and the linker may have affinity for each other, and for example, the linker may be any material being capable of changing the structure in contact with the biological material.

For example, the linker for bind the metal nanoparticle may have one terminal end that is substituted with a thiol, a thioether, a thiourea, a phosphorothiate, a thiocarbamate, an amine, a histidine, a phosphine, a phosphite residual group, and the like.

For example, the other terminal end of the linker for binding the light emitting material may be substituted with biotin, avidin, HIS-tag, Ni-NTA (Nickel Nitrilotriacetic acid), N-hydroxysuccinmide, amine, thiol, histidine, phosphine, aldehyde tag, hydrazide tag, halide, alkyne, azide, HALO tag, benzylguanine, SNAP-tag, benzylcytosine, CLIP-tag, FLAG-tag, or maleimide. DeletedTextsNickel Nitrilotriacetic acid)

In order to be linked with the linker, the light emitting material may be coated with a material such as biotin, avidin, HIS-tag, Ni-NTA (Nickel Nitrilotriacetic acid), N-hydroxysuccinmide, amine, thiol, histidine, phosphine, aldehyde tag, hydrazide tag, halide, alkyne, azide, Halo tag, benzylguanine, SNAP-tag, benzylcytosine, CLIP-tag, FLAG-tag, or maleimide.

For example, the semiconductor nanocrystal as the light-emitting material is coated with avidin and may be connected with a linker having one terminal end substituted with biotin.

Each terminal end of the linker is substituted with a material subject to be respectively bound with the light emitting material and the metal nanoparticle, but the material is not limited to the aforementioned materials.

For example, the linker having one terminal end substituted with a thiol group (—SH) and the other terminal end substituted with biotin is respectively reacted with the light emitting material, or the metal nanoparticle. Then, the produced conjugate is reacted with the rest of the metal nanoparticle or the light emitting material, obtaining a conjugate of "nanoparticle-linker-light emitting material".

Figure 2:
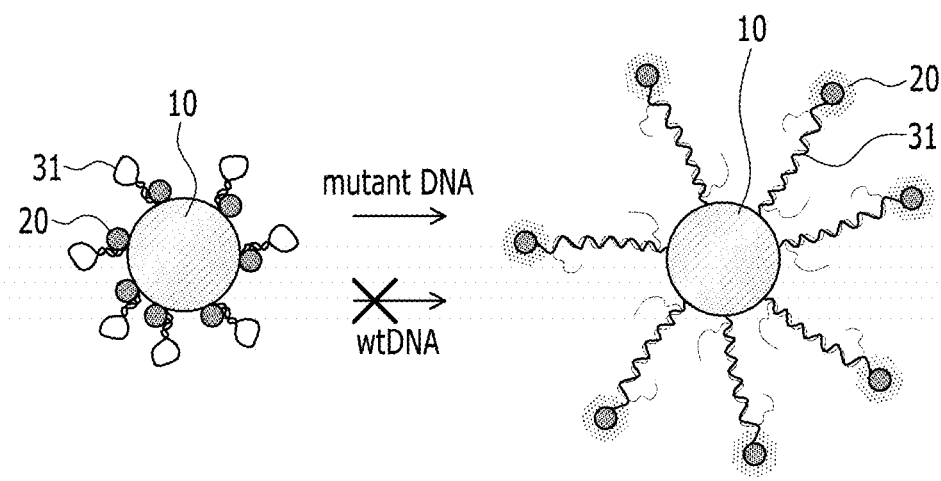
FIG. 2 is a schematic view showing that the conjugate of a metal nanoparticle (10) and a light emitting material (20) according to the embodiment is linked by a DNA having a hairpin structure (31) and thus does not contact a biological material (left) and that the conjugate contacts the specific biological material, which changes the structure of the DNA having a hairpin structure and makes the light emitting material fluorescent (right).

According to an exemplary embodiment, the linker may be a DNA having a hairpin structure. As shown in FIG. 2, due to the characteristic structure of the DNA having a hairpin structure, the light emitting material and the metal nanocrystal that are respectively bound at both terminal ends thereof are still close each other. Accordingly, the metal nanocrystal absorbs fluorescence of the light emitting material, and the light emitting material does not emit light. However, when this conjugate contacts a biological sample including a specific biological material, for which the DNA having a hairpin structure has affinity, the DNA having a hairpin structure is conjugated with the specific biological material, and may change its hairpin structure.

The bent hairpin structure of the DNA may become unfolded due to conjugation with the biological material. As a result, the light emitting material and the metal nanoparticle conjugated at both terminal ends of the hairpin DNA may not be close but become far apart from each other. Accordingly, the extinct light emitting material may emit light and become fluorescent. This fluorescence may be measured to detect concentration of the specific biological material in the sample.

FIG. 1 is a schematic view showing a conjugate of a metal nanoparticle including a magnetic core (11) and a light emitting material (20) that are conjugated through a linker (30) according to one embodiment. In the schematic view, the metal nanoparticle (10) includes a layer (13) such as a metal oxide layer or a polymer layer between the magnetic core (11) and a metal shell (12) thereon. The linker (30) is unfolded in the conjugate, and accordingly, the light emitting material (20) bound to the linker (30) is far apart from the metal nanoparticle (10) and emits light.

FIG. 2 is a schematic view showing a mechanism of a conjugate of a metal nanoparticle (10) including a magnetic core with a plurality of light emitting materials through a linker according to one embodiment of the present invention. Specifically, FIG. 2 shows mechanism of a conjugate including DNA having a hairpin structure (31) as a linker, in which the DNA having a hairpin structure (31) is designed to have affinity for mutant DNA. When the conjugate contacts with the mutant DNA in a sample, the hairpin structure in the conjugate becomes unfolded as shown in the right drawing of FIG. 2. In this case, the light emitting material (20) bound at one end of the hairpain DNA emits light. However, if the sample has no the mutant DNA but has wild DNA having at least one different base sequence from that of the mutant DNA, the hairpin DNA has no affinity for the wild DNA and is not deformed as shown in the right drawing of FIG. 2 but maintains a state shown in the left drawing of FIG. 2. As shown in left drawing of FIG. 2, the light emitting material (20) is close to the metal nanoparticle (10) due to the DNA having a hairpin structure, and the metal nanoparticle quenches light emission of the light emitting material.

In other words, the DNA having a hairpin structure as the linker may be adjusted regarding base sequence and the like to detect a biological material and measure its concentration, so that the hairpin structure of the DNA is changed in contact with the biological material to control light emission of the light emitting material linked to the linker. In other words, when the conjugate contacts with the mutant DNA and the structure of the linker is changed, luminance intensity of the conjugate may be changed. The luminance intensity may be measured to detect existence of a specific biological material in a sample and measure its concentration.

In another exemplary embodiment, the linker may be single strand DNA. The single strand DNA may have a base sequence being capable of forming a complementary bond with a base sequence of a specific DNA in a biological sample to be detected. When the single strand DNA is used as a linker, a conjugate including the linker contacts a biological sample, in which another single strand DNA being capable of forming a complementary bond with the linker is present, the linker forms a complementary bond with the single strand DNA in the biological sample, and thus the structure of the linker may be changed. Due to such a change of the linker, the conjugate does not emit light but may be changed to a form of emitting light, while the conjugate emits light but may be changed to become extinct.

However, when the specific biological material exists at a very low concentration in the sample, light may be emitted from a light emitting material due to the structure change of the linker, but may be too weak to be detected.

On the contrary, the conjugate according to the embodiment may be concentrated using a magnetic force, and the concentrated conjugate may be used to sufficiently detect fluorescence of the light emitting material of the conjugate, by including a magnetic core in the metal nanoparticle even if the specific biological material exists at a very low concentration in the sample.

Accordingly, the conjugate according to the embodiment may not only detect the specific biological material in the biological sample but may be also easily separated and concentrated to highly sensitively detect the specific biological material existing at a very low concentration.

The linker may be designed to have a specific structure by adjusting a base sequence or a peptide structure depending on biological features of the biological material to be detected such as a base sequence or an amino acid sequence. Accordingly, a metal nanoparticle and a light emitting material that are bound at both terminal ends of the linker become far apart from each other or close to each other due to structural changes of the linker in contact with the specific biological material in the biological sample.

Accordingly, the conjugate according to the embodiment may include any linker that may be bound with a metal nanoparticle including a magnetic core, and a light emitting material at both terminal ends, makes the light emitting material and the metal nanoparticle close to each other or far apart from each other and thereby makes fluorescence of the light emitting material be extinct or emit when they are bound with the linker, and makes the light emitting material and the metal nanoparticle far apart from each other or close to each other due to change of the linker and thereby makes fluorescence of the light emitting material emit or be extinct when such a conjugate contacts a biological material to be detected.

In addition, the linker may have any length if it makes fluorescence of the light emitting material emit or not emit depending on a structural difference between contacting and not contacting a specific biological material. The linker may have a length of about 3 nm to about 100 nm, for example, about 10 nm to about 90 nm, and for another example, about 20 nm to about 80 nm, without limitation.

In another embodiment, a biosensor including the conjugate of a metal nanoparticle and a light emitting material according to the embodiment is provided.

As described above, the conjugate of a metal nanoparticle and a light emitting material according to the embodiment may be used for measuring and analyzing the existence and concentration of a specific biological material in a biological sample, and may function as a biosensor. As described above, by contacting a biological sample to detect existence and concentration of a specific biological material with the conjugate, existence and/or concentration of a specific biological material in the sample may be confirmed and analyzed, and therefore the conjugate itself may function as a high sensitive biosensor.

Furthermore, the biosensor may further include a substrate supporting the conjugate of a metal nanoparticle and a light emitting material.

The substrate may be transparent or opaque, and may be made of an inorganic material or an organic material.

Herein, the substrate may be transparent or opaque, and when it is a transparent substrate, light emission of the biosensor on the transparent substrate may be measured, while when it is an opaque substrate, light emission of the biosensor on the opaque substrate may be measured measuring device using a reflective mode.

The transparent substrate may include an inorganic material substrate such as glass, ITO (Indium Tin Oxide), quartz, alumina, silicon, carbon materials, and the like, or an organic material substrate made of a transparent polymer. The opaque substrate may include a paper, an opaque glass, or an opaque polymer substrate. The substrate is not limited, but may include any substrate as long as it is good for easily measuring light emission of a biosensor supported thereon but has neither a particular chemical reaction with a material including the biosensor nor a chemical reaction with a biological material or a biological sample for the measurement.

In addition, the substrate may consist of a material having magnetism or include a material having magnetism at the inside or the bottom. When the substrate includes a material having magnetism, the substrate is bonded with the conjugate through the magnetism.

Alternatively, the conjugate of a metal nanoparticle and a light emitting material may be bonded with the substrate through a chemical reaction. For example, the substrate and the light emitting material respectively include a substituent capable of being bonded each other on the surface, and the substituents may be bonded one another and bond the conjugate and the substrate. For example, the same substituent as the substituent substituted at the terminal end of the linker may be substituted on the surface of the substrate to bond the light emitting material with the linker, and thus, the light emitting material may be bonded with the substrate as well as the linker.

Examples of such a chemical bond may be a bond between SNAP and benzylguanine, a bond between histag and Ni-NTA, a bond between CLIP-tag and benzylcytosine, a bond between Halotag and an alkylhalide, a bond between maleimide and thiol, but are not limited thereto.

On the other hand, when a quartz substrate is used, a chemical bond using a silicon oxide in the substrate itself may be used.

When the biosensor consists of the conjugate of a metal nanoparticle and a light emitting material, the biosensor may be present in a form of a powder including the conjugate or in a form of a solution including the conjugate. When the biosensor further includes the substrate, the conjugate may be variously bonded on the substrate in the biosensor. This biosensor may be contacted with a biological sample including a specific biological material to detect presence and/or concentration of the specific biological material in the biological sample by putting the biosensor in the biological sample or flowing the biological sample in a predetermined amount on the surface of the biosensor and then, measuring light emission changes of the biosensor after a predetermined time. When the biosensor is included in the biological sample but does not sense light emission changes after a predetermined time, existence and/or concentration of a specific biological material present in a small amount may be measured by concentrating and separating the biosensor in the sample with magnetism and measuring light emission degree of the biosensor.

In another embodiment of the present invention, a method of measuring the concentration of a specific biological material in a biological sample, which includes contacting the conjugate of a metal nanoparticle and a light emitting material or biosensor according to the embodiment with the biological sample, is provided.

The method of measuring the concentration of a biological material may further include measuring light emission or light absorption of the light emitting material after contacting the conjugate or the biosensor with the biological sample.

Light emission or light absorption of the conjugate or the biosensor may be measured by using a well-known and appropriate optical apparatus depending on each light emitting material. For example, the optical apparatus may include EM-CCD, a CMOS-detector, an Avalanche Photodiode Detector (APD), a photon multiplier tube (PMT), a fluorometer, an optical microscope, and the like but may include any common optical apparatus well-known in a related art.

The method of measuring the concentration of a biological material may further include concentrating the conjugate or the biosensor using magnetism, before measuring light emission or light absorption of the light emitting material.

The biological material may be an enzyme, an antigen, an antibody, a protein, a peptide, a hydrocarbon material (a carbohydrate), DNA, RNA, a part thereof, or a combination thereof, and for example, a biomarker of a disease.

The biological material may include, for example, a disease biomarker. The concentration of the biological material may be measured to obtain information of the disease by contacting the conjugate or the biosensor with the biological sample including the biological material and measuring light emission or light absorption of the conjugate or the biosensor.

In another embodiment, provided is a method of obtaining information for a specific disease ex vivo that includes contacting the conjugate or the biosensor with a biological sample.

A method of measuring the existence or concentration of the biological material and a method of obtaining information for a disease may be performed in vitro or in vivo.

For example, the concentration of the specific biological material may be measured by contacting the conjugate or the biosensor according to the embodiment with blood, urine, saliva, and the like sampled from a patient, and measuring a light emission or light absorption degree of the conjugate or the biosensor in the sample.

In addition, the conjugate or the biosensor according to the embodiment is externally measured regarding fluorescence degree after injecting the conjugate or the biosensor into, for example, an artery or vein, the liver, stomach, the small intestine, the large intestine, or the pancreas of a patient.

Hereinafter, the present invention is illustrated in more detail with reference to examples. However, these examples are exemplary embodiments of the present invention, and the present invention is not limited thereto.

Example 1

Preparation of Metal Nanoparticle-Semiconductor Nanocrystal Conjugate Using ssDNA Preparation Example 1-1

Preparation of Semiconductor Nanocrystals Coated with Streptavidin 3 mL of a semiconductor nanocrystal (Invitrogen, 605, Q1 0101 MP) (200 nM) dissolved in chloroform, a 0.3 M TBAB (Tetra-n-butylammonium bromide) chloroform solution, and 180 µL of mPEGthiol ($CH_3O\,(CH_2CH_2O)_n CH_2CH_2SH$) are mixed for 30 minutes. Then, 4 mL of a 0.2 M NaOH aqueous solution is added thereto, and the mixture is vortexed and centrifuged to separate layers. Among the layers, a water layer is taken and filtered with a centrifuge filter (30 kDa, Amicon) to obtain a water-soluble semiconductor nanocrystal, and the water-soluble semiconductor nanocrystal is purified through an NAP desalting column (produced by "GE Healthcare"). Herein, Tris 10 mM (T30) including 30 mM NaCl is used as a buffer solution.

200 nM of the semiconductor nanocrystal is dissolved in the T30 buffer, and 100 µL of the solution is reacted with $SHC_{11}H_{23}(OCH_2CH_2)_{12}$—$OCH_2COOH$ (Prochimia) in 105 times as much amount as the solution for 2 hours, and then, PEG not reacting with the semiconductor nanocrystal is removed through an NAP-5 column. Then, the obtained product is reacted with 3.3 µL of 60 µm His-tagged streptavidin (produced by "abcam") for 2 hours and then, electrodialyzed in a microFloat-A-lyzer (MWCO 100 kDa, Spectra/Por) at 100 V for 10 minutes, removing His-Streptavidin not binding with the semiconductor nanocrystal. The obtained semiconductor nanocrystal-Streptavidin solution is stored at 4° C. until it is used.

Preparation Example 1-2

Preparation of Metal Nanoparticles Conjugated with ssDNA

A linear single strand DNA (ssDNA) of 42 mers (SEQ ID NO: 1), in which a thiol at the 3' end and a biotin at the 5' end are substituted, 5'-biotin CCG GCG GCC CTA ATC GAG TTT CAC GTC CTA GAC CGC GCC CGG-thiol 3', is used as a linker. 2.86 µL of the ssDNA 93.6 µM is reacted with bis(p-sulfonatophenyl)phenylphosphine disodium salt (BSPP) for 10 minutes to reduce the thiol (—SH) group at the terminal end 3'. This ssDNA solution is added to a T2O buffer (10 mM Tris, pH 8, 20 mM NaCl) including the metal nanoparticle $Zn_{0.4}Fe_{2.6}O_4@SiO_2@Au$ (0.56 nM, 90 µL) including a zinc/iron oxide magnetic core, silica shell, and gold shell, and reacted therewith over one night. Subsequently, $SHC_{11}H_{23}(OCH_2CH_2)OCH_2COOH$ (10 mM, 0.5 µL) is added thereto, and the mixture is reacted in a shaker for 5 hours. This ssDNA-metal nanoparticle conjugate is purified through a Mini-MACS (Miltenyl Biotech) column and stored at 4° C.

Preparation Example 1-3

Conjugation of a Metal Nanoparticle and Semiconductor Nanocrystals

Figure 3:
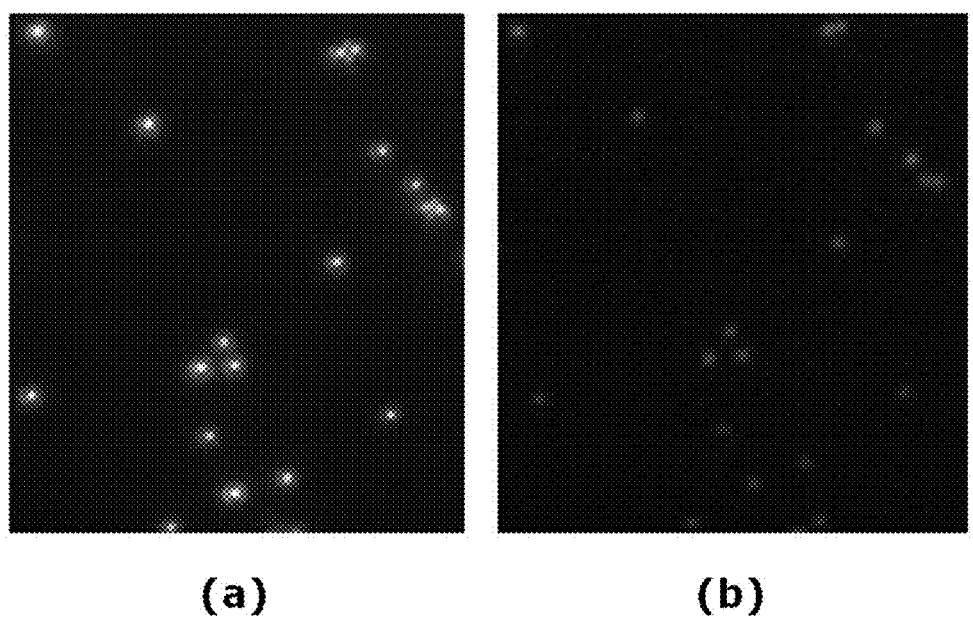
FIGS. 3(a) and 3(b) are images of an optical microscope (Reflective dark field microscopy) and a fluorescence microscope (TRIF) of the conjugate of the metal nanoparticle and the semiconductor nanocrystal prepared according to Preparation Example 1-4, on a substrate.

A metal nanoparticle (50 fmol in T30 buffer) conjugate with the ssDNA substituted with biotin at one terminal end prepared in Preparation Example 1-2 is mixed with the semiconductor nanocrystal (5 pmol, 1 µM) coated with streptavidin on its surface prepared in Preparation Example 1-1 for 30 minutes. The resulting metal nanoparticle-semiconductor nanocrystal conjugate is separated with agarose gel electrophoresis at 200 V for 15 minutes. Among the conjugates, when a conjugate in which the metal nanoparticle and the semiconductor nanocrystal are bonded in a ratio of 1:1 is separated and put on a biotin coated glass substrate and then, simultaneously examined by using an optical microscope (Reflective dark field microscopy) and a fluorescence microscope (TRIF microscopy), it is confirmed that the semiconductor nanocrystal and the metal nanoparticle have a bonding structure, since fluorescence appears at the position that scattering of the metal nanoparticle appears (refer to FIG. 3).

Example 2

Preparation of Metal Nanoparticle-Semiconductor Nanocrystal Conjugates using a Hairpin-structured DNA Linker Preparation Example 2-1

Preparation of Conjugates of a Metal Nanoparticle and Hairpin DNAs

Hairpin oligonucleotide (SEQ ID NO: 2) having thiol (—SH) and biotin respectively substituted at each 5' and 3' terminal end (biotin-TTTTTGAT TTT GGG CGG GCC AAA CTG TTG GCC CGTTTACTGACTGACTG-thiol, Integrated DNA Technology, Inc.) is used as a linker. The hairpin oligonucleotide (93.6 µM, 2.86 µL) is reacted with bis(p-sulfonatophenyl)phenylphosphine disodium salt (BSPP) for 10 minutes to reduce the thiol (—SH) group at the 5' terminal end. This hairpin oligonucleotide solution is added to a $T_2O$ buffer (10 mM Tris, pH 8, 20 mM NaCl) including the metal nanoparticle $Zn_{0.4}Fe_{2.6}O_4@SiO_2@Au$ (0.56 nM, 90 μL) including a zinc/iron oxide magnetic core, silica shell, and gold shell, and the mixture is reacted for one night. Next, SHC$_{11}$H$_{23}$(OCH$_2$CH$_2$)OCH$_2$COOH (10 mM, 0.5 μL) is added to the reacted mixture. The resulting mixture is reacted for 5 hours in a shaker. The produced DNA-metal nanoparticle conjugate therein is purified through a Mini-MACS column (Miltenyi Biotech Inc.) and stored at 4° C.

Figure 4:
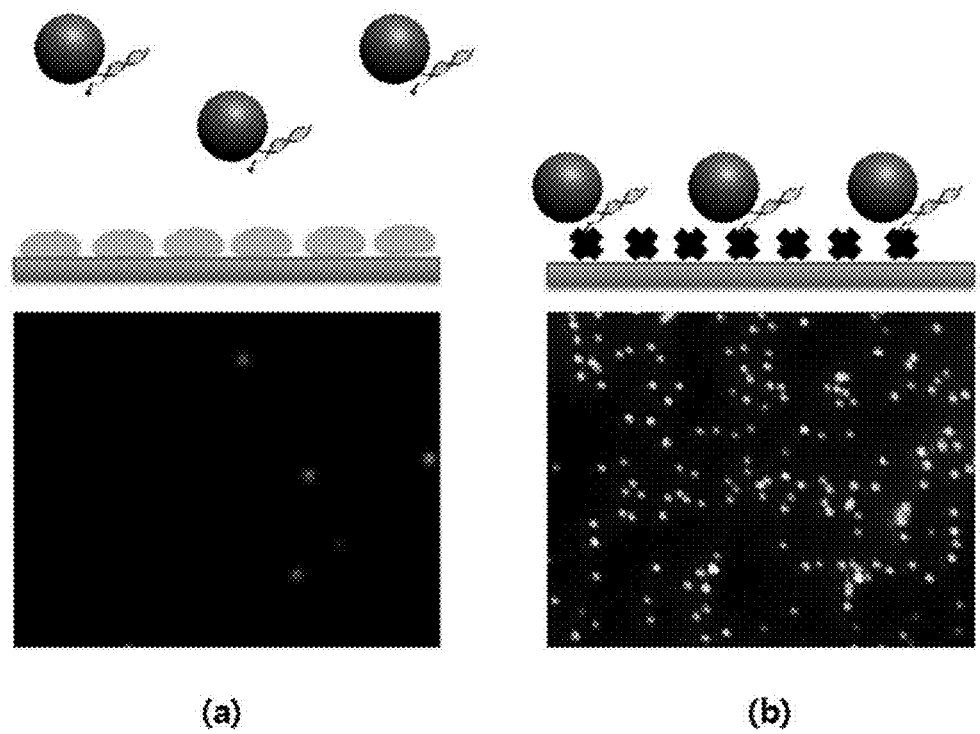
FIG. 4 is a dark field microscopic image showing each a conjugate of a DNA having a hairpin structure and being substituted with a biotin at one end and metal nanoparticle according to Preparation Example 2-1 put in a glass flow chamber coated with BSA (bivine serum albumin) (FIG. 4(a)) or in another glass flow chamber coated with streptavidin (FIG. 4(b)).

When the DNA-metal nanoparticle conjugate is put in a glass flow chamber coated with bovine serum albumin (BSA) or streptavidin (stv), the DNA-metal nanoparticle conjugate has no specific binding bond on the surface of a substrate coated with BSA (FIG. 4(a)) but has high affinity on the surface of a substrate coated with streptavidin, showing that the conjugate is well bound with biotinylated DNA (FIG. 4(b)).

Preparation Example 2-2

Preparation of Conjugate of Metal Nanoparticle and Semiconductor Nanocrystal

Figure 5:
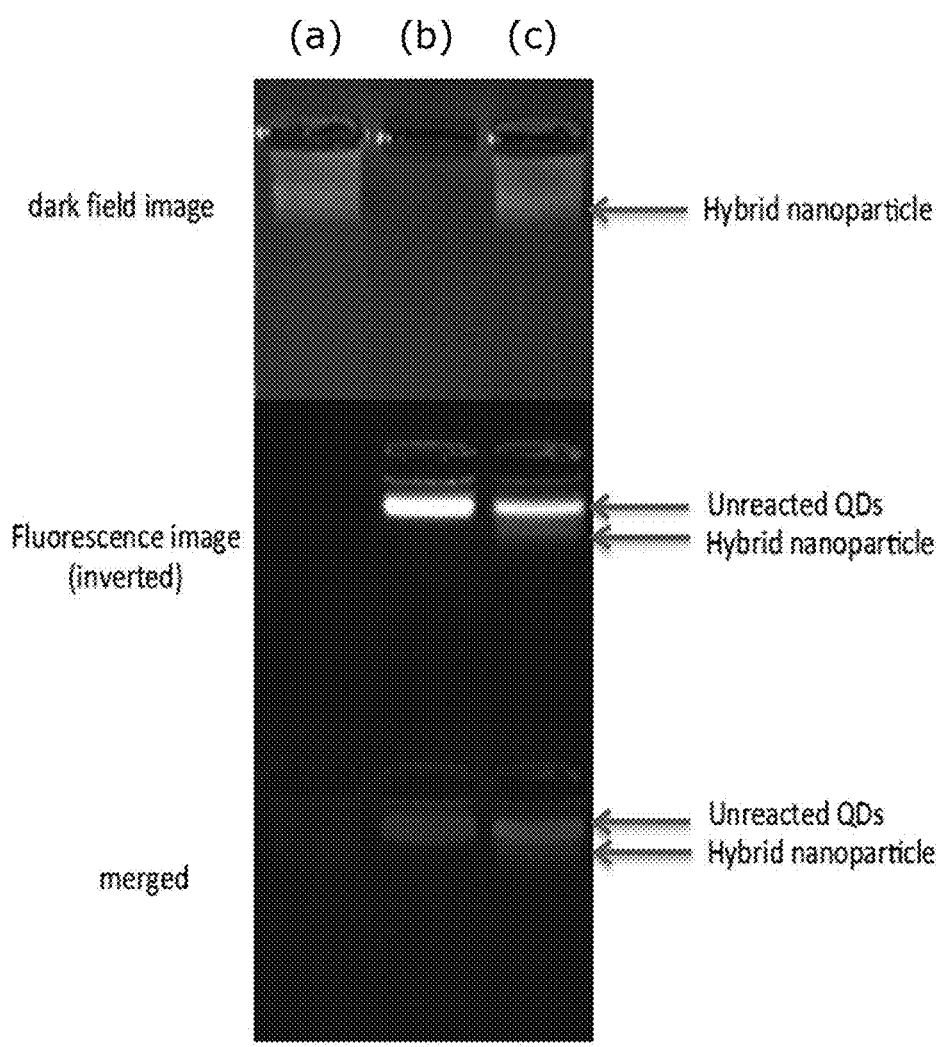
FIG. 5 is dark field images, fluorescence images (inverted) and merged images of the dark field images and fluorescence images of the DNA having a hairpin structure-metal nanoparticle conjugate that is prepared in Preparation Example 2-1 (a), the semiconductor nanocrystal coated with streptavidin that is prepared in Preparation Example 1-1 (b), and the conjugate of a metal nanoparticle and a semiconductor nanocrystal that is prepared in Preparation Example 2-2 (c).
Figure 6:
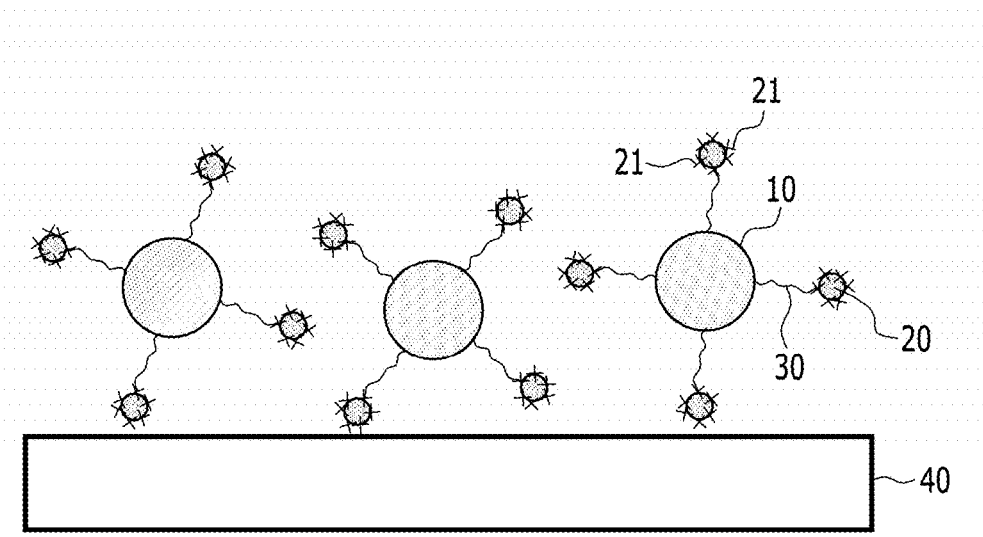
FIG. 6 is a schematic view of a structure of the biosensor according to Example 4, which is fixed on a biotinylated glass substrate. The biosensor includes a conjugate of a magnetic/metal nanoparticle (10) and a semiconductor nanocrystal (20) linked with a linear ssDNA. The semiconductor nanocrystal (20) is coated with streptavidin (21).

A streptavidin-coated semiconductor nanocrystal prepared in Preparation Example 1-1 is used at 100 times as many moles as the hairpin DNA-metal nanoparticle conjugate (a Zn$_{0.4}$Fe$_{2.6}$O$_4$@SiO$_2$@Au-hairpin DNA nanoparticle solution (50 fmol in T30)) prepared in Preparation Example 2-1, and the mixture is reacted in a shaker for 3 hours. The conjugation of the semiconductor nanocrystal with the Zn$_{0.4}$Fe$_{2.6}$O$_4$@SiO$_2$@Au nanoparticle is checked through electrophoresis (FIG. 5(c)).

Example 3

Preparation of Metal Nanoparticle-Fluorescent Dye Conjugate

Alex 555-conjugated streptavidin (Invitrogen) as a fluorescent dye is used at 100 times as many moles as the hairpin DNA-metal nanoparticle conjugate (a Zn$_{0.4}$Fe$_{2.6}$O$_4$@SiO$_2$@Au-hairpin DNA nanoparticle solution (50 fmol in T30)) according to Preparation Example 2-1, and the mixture is reacted in a shaker for 3 hours. The conjugation of the Zn$_{0.4}$Fe$_{2.6}$O$_4$@SiO$_2$@Au nanoparticle with the Alex 555-conjugated streptavidin is checked through electrophoresis.

Example 4

Figure 7:
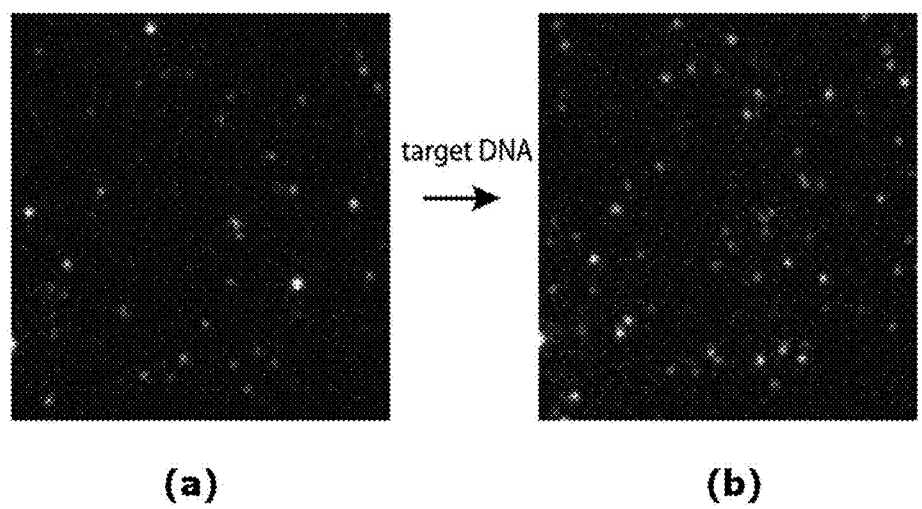
FIG. 7 is fluorescence microscope images before contacting a target DNA (a) and after contacting a target DNA (b) with the biosensor according to Example 4.
Figure 8:
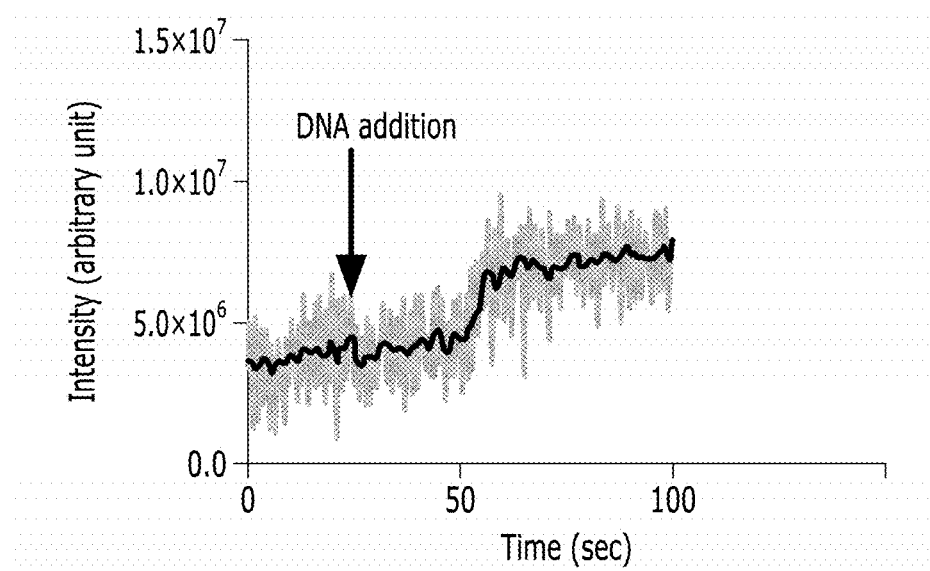
FIG. 8 shows changes of fluorescent intensities before contacting a target DNA and after contacting a target DNA with the biosensor according to Example 4.

Manufacture of Biosensor using Magnetic Material/Conjugate of Metal Nanoparticle and Semiconductor Nanocrystal A conjugate of a magnetic/metal nanoparticle and a semiconductor nanocrystal linked by a linear ssDNA 42 mers (SEQ ID NO: 1) (5'-biotin CCG GCG GCC CTA ATC GAG TTT CAC GTC CTA GAC CGC GCC CGG-thiol 3') according to Example 1 is put and fixed on a biotinylated glass substrate. 1 nM of a target ssDNA having a complementary sequence to the ssDNA of the linker is added to the substrate, and fluorescence change of the semiconductor nanocrystal is examined with the homemade TIRF microscopy equipped with EM-CCD. The fluorescence of the semiconductor nanocrystal increases after adding the target DNA (FIGS. 7 and 8), and the reason is that the target DNA is bonded with the linker DNA between the metal nanoparticle and the semiconductor nanocrystal and increases a distance between the metal nanoparticle and the semiconductor nanocrystal.

While this disclosure has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A conjugate of a metal nanoparticle and a light emitting material, comprising
    a metal nanoparticle consisting of a magnetic core, a metal shell on a surface of the magnetic core, and a dielectric layer interposed between the magnetic core and the metal shell,
    a light emitting material, and
    a linker bound to the metal shell on the surface of the metal nanoparticle, wherein the linker links the metal nanoparticle to the light emitting material and has an affinity for a biological material,
    wherein the magnetic core is $Zn_{0.4}Fe_{2.6}O_4$,
    wherein the light emitting material is a semiconductor nanocrystal, and
    wherein the metal nanoparticle and the light emitting material are conjugated in a ratio of 1:1 through the linker.

2. The conjugate of claim 1, wherein the dielectric layer is a metal oxide or a polymer.

3. The conjugate of claim 1, wherein the dielectric layer comprises $SiO_2$, $TiO_2$, $ZrO_2$, $Al_2O_3$, $Cu_xO$ (0<x<2), or a combination thereof.

4. The conjugate of claim 1, wherein the metal shell is a metal shell selected from gold, silver, copper, platinum, and an alloy thereof.

5. The conjugate of claim 1, wherein the metal nanoparticle and the light emitting material are in close proximity to each other such that light emission of the light emitting material is quenched.

6. The conjugate of claim 1, wherein the metal nanoparticle and the light emitting material are a far distance away from each other such that the light emitting material is capable of emitting light.

7. The conjugate of claim 6, wherein when the linker is contacted with a specific biological material the structure of the linker is changed such that light emission of the light emitting material is quenched.

8. The conjugate of claim 1, wherein the linker is DNA, single strand DNA (ssDNA), RNA, a protein, a peptide, an antigen, an antibody, an enzyme, a hydrocarbon material (a carbohydrate), a fragment thereof, or a combination thereof.

9. The conjugate of claim 1, wherein the linker is a DNA having a hairpin structure or a single strand DNA.

10. The conjugate of claim 1, wherein the linker has a length of about 3 nm to about 100 nm.

11. The conjugate of claim 1, wherein the linker has both terminal ends that are substituted with respective functional groups to bind the metal nanoparticle and the light emitting material.

12. The conjugate of claim 1, wherein the linker has one terminal end that is substituted with thiol, thioether, thiourea, phosphorothiate, thiocarbamate, amine, histidine, phosphine, or phosphate.

13. The conjugate of claim 1, wherein one terminal end of the linker for binding the light emitting material is substituted with biotin, avidin, His-tag, Ni-NTA, N-hydroxysuccinmide, amine, thiol, histidine, phosphine, aldehyde tag, hydrazide tag, halide, alkyne, azide, benzylguanine, benzylcytosine, or maleimide.

14. The conjugate of claim 1, wherein the light emitting material is coated with avidin, HIS-tag, Ni-NTA, N-hydroxysuccinmide, amine, thiol, histidine, phosphine, aldehyde tag, hydrazide tag, halide, alkyne, azide, benzylguanine, benzylcytosine, or maleimide.

15. The conjugate of claim 1, wherein the biological material for which the linker has affinity is an enzyme, an antigen, an antibody, a protein, a peptide, DNA, RNA, a carbohydrate, a fragment thereof, or a combination thereof.

16. The conjugate of claim 1, wherein the biological material for which the linker has affinity is a biomarker of a disease.

17. The conjugate of claim 1, wherein the metal nanoparticle has a diameter of about 5 nm to about 200 nm.

18. The conjugate of claim 1, wherein the light emitting material has a diameter of about 2 nm to about 30 nm.

19. The conjugate of claim 1, the metal shell is gold shell, and the dielectric layer is silica shell.

20. The conjugate of claim 1, wherein the dielectric layer comprises $TiO_2$, $ZrO_2$, $Al_2O_3$, $Cu_xO$ (0<x<2), or a combination thereof.

21. A biosensor comprising the conjugate of a metal nanoparticle and a light emitting material of claim 1 and a substrate supporting the conjugate of a metal nanoparticle and a light emitting material.

22. The biosensor of claim 21, wherein the substrate is selected from glass, ITO (Indium Tin Oxide), quartz, alumina, polymer, silicon, carbon materials or paper.

23. The biosensor of claim 22, wherein the conjugate of a metal nanoparticle and a light emitting material is supported on the substrate by a bond through a chemical reaction or magnetism.

24. A method of measuring the concentration of a specific biological material in a biological sample, comprising:
    contacting the conjugate of a metal nanoparticle and a light emitting material of claim 1 with the biological sample and
    measuring light emission or light absorption of the light emitting material after contacting the conjugate or the biosensor with the biological sample.

25. The method of claim 24, which further comprises concentrating the conjugate or the biosensor by applying a magnetic force, before measuring light emission or light absorption of the light emitting material.

* * * * *

SEQUENCE LISTING

```
<160> NUMBER OF SEQ ID NOS: 2

<210> SEQ ID NO 1
<211> LENGTH: 42
<212> TYPE: DNA
<213> ORGANISM: Artificial Sequence
<220> FEATURE:
<223> OTHER INFORMATION: synthesized ssDNA

<400> SEQUENCE: 1
ccggcggccc taatcgagtt tcacgtccta gaccgcgccc gg                          42

<210> SEQ ID NO 2
<211> LENGTH: 49
<212> TYPE: DNA
<213> ORGANISM: Artificial Sequence
<220> FEATURE:
<223> OTHER INFORMATION: synthesized hairpin DNA

<400> SEQUENCE: 2
tttttgattt tgggcgggcc aaactgttgg cccgtttact gactgactg                   49
```